(12) United States Patent
Yonezu et al.

(10) Patent No.: US 9,957,873 B2
(45) Date of Patent: May 1, 2018

(54) SENSOR

(71) Applicant: NGK SPARK PLUG CO., LTD., Nagoya-shi, Aichi (JP)

(72) Inventors: Kunihiko Yonezu, Inuyama (JP); Takehiro Oba, Kounan (JP); Hisaharu Nishio, Tokai (JP); Ginjiro Ito, Nagoya (JP); Yuichi Yamada, Komaki (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 224 days.

(21) Appl. No.: 14/990,947

(22) Filed: Jan. 8, 2016

(65) Prior Publication Data

US 2016/0201542 A1    Jul. 14, 2016

(30) Foreign Application Priority Data

Jan. 9, 2015   (JP) ................................. 2015-002893
Oct. 15, 2015  (JP) ................................. 2015-203455

(51) Int. Cl.

| G01N 27/407 | (2006.01) |
|---|---|
| F01N 11/00 | (2006.01) |
| G01N 27/406 | (2006.01) |
| F02M 35/10 | (2006.01) |
| F02M 57/00 | (2006.01) |

(52) U.S. Cl.
CPC ......... *F01N 11/007* (2013.01); *G01N 27/406* (2013.01); *G01N 27/4062* (2013.01); *F02M 35/10373* (2013.01); *F02M 57/005* (2013.01); *G01N 27/4078* (2013.01)

(58) Field of Classification Search
CPC ....... G01N 27/4062; F01N 2560/02–2560/028
See application file for complete search history.

(56) References Cited

U.S. PATENT DOCUMENTS

| 6,068,746 A | 5/2000 | Kojima et al. | |
|---|---|---|---|
| 6,477,887 B1 * | 11/2002 | Ozawa | G01N 27/4075 204/424 |
| 2014/0020446 A1 * | 1/2014 | Yonezu | G01N 33/0009 73/23.2 |

FOREIGN PATENT DOCUMENTS

| JP | 3873390 B2 | 1/2007 |
|---|---|---|
| JP | 2014-002132 A | 1/2014 |

(Continued)

*Primary Examiner* — Alexander S Noguerola
(74) *Attorney, Agent, or Firm* — Stites & Harbison, PLLC; Jeffrey A. Haeberlin; James R. Hayne

(57) ABSTRACT

A sensor includes a detector element including a detecting portion and an element back portion on which two or more electrical connection terminal portions are formed; two or more connection terminals which each include an oblong frame main body that extends in an axial direction and an element contact portion that is electrically connected to a corresponding one of the electrical connection terminal portions; a separator that accommodates the connection terminals and the element back portion; and a base that surrounds an outer periphery of the separator. The separator includes a partition wall that is made of a resin material and partitions a plurality of accommodation spaces from each other. The accommodation spaces include an element accommodation space that accommodates portions of the element contact portions and the element back portion, and a plurality of terminal accommodation spaces which each accommodate one of the two or more frame main bodies.

8 Claims, 11 Drawing Sheets

(56) References Cited

FOREIGN PATENT DOCUMENTS

JP           2014-38083 A     2/2014
WO        WO 01/34951 A2 *   5/2001     ............. F01N 11/00

\* cited by examiner

FIG. 12
(a)
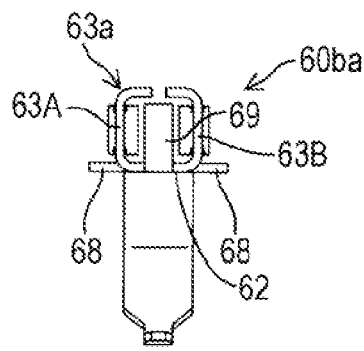
(b)
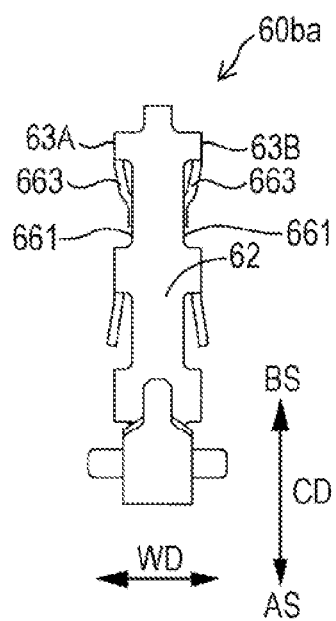
(c)
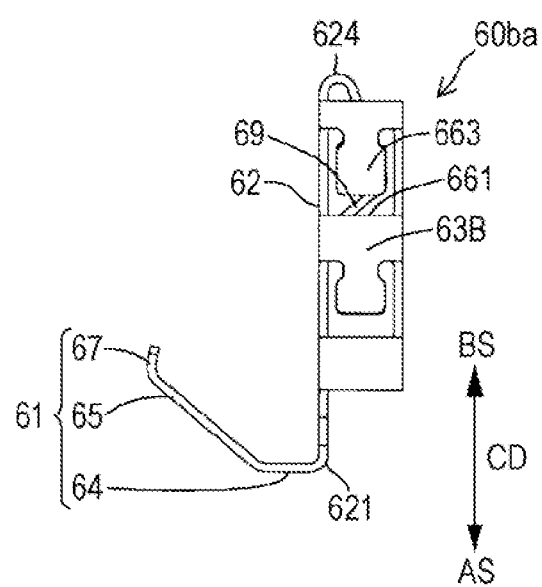

SENSOR

BACKGROUND OF THE INVENTION

Field of the Invention

The present invention relates to a sensor technology.

Description of the Related Art

Examples of known sensors are attached to an inlet system (for example, an intake pipe or intake manifold) or an exhaust system of an internal combustion engine, such as a diesel engine or a gasoline engine, to detect the concentration of a specific gas component (for example, oxygen or Nox) contained in measurement target gas (see, for example, PTL 1 and PTL 2). The sensor disclosed in PTL 1 includes a detector element, connection terminals that are electrically connected to the detector element, and a separator that accommodates a back portion of the detector element and the connection terminals. A detection signal output from the detector element is output to the outside through the connection terminals. The concentration of the specific gas is calculated on the basis of the detection signal by an external device.

CITATION LIST

Patent Literature

PTL 1 is Japanese Unexamined Patent Application Publication No. 2014-2132.

PTL 2 is Japanese Patent No. 3873390.

BRIEF SUMMARY OF INVENTION

The separator included in the sensor described in PTL 1 is made of a ceramic material. In this case, the separator needs to be attached to the sensor as a component thereof by, for example, fixing a metal retainer, which supports the separator, to an outer cylinder by crimping and attaching the outer cylinder to a metal shell. Thus, when the separator made of a ceramic material is used as a component of the sensor, the manufacturing costs and the number of manufacturing steps of the sensor are increased. When the separator is made of a ceramic material, there is also a problem that the weight of the sensor is increased.

A sensor in which the separator is formed of a resin material, as in the sensor according to PTL 2, has a problem that the strength of the separator is lower than that made of a ceramic material. In addition, according to the technology described in PTL 2, a connector that is electrically connected to the detector element extends in an axial direction of the detector element. Therefore, there is a problem that the sensor is large in the axial direction. When the sensor is large in the axial direction, it may be difficult to attach the sensor depending on the location where the sensor is to be attached.

The present invention has been made to solve the above-described problems, and may be realized by the following embodiments or applications.

(1) According to an aspect of the present invention, a sensor includes a detector element that extends in an axial direction and has a shape of a plate having two opposing principal surfaces, the detector element including a detecting portion at a front side in the axial direction and an element back portion at a back side in the axial direction, the detecting portion detecting a specific gas component contained in measurement target gas, the element back portion having two or more electrical connection terminal portions formed on one of the principal surfaces; two or more connection terminals which each include an oblong frame main body that extends in the axial direction and an element contact portion that is bent at a front end portion of the frame main body so as to extend toward the back side and that is electrically connected to a corresponding one of the electrical connection terminal portions; a separator that accommodates the connection terminals and the element back portion; and a base that surrounds an outer periphery of the separator. In this sensor, the separator includes a partition wall that is made of a resin material and partitions a plurality of accommodation spaces from each other, and the accommodation spaces include an element accommodation space that accommodates portions of the element contact portions and the element back portion, and a plurality of terminal accommodation spaces which each accommodate one of the two or more frame main bodies.

According to the sensor of this aspect, the separator includes the partition wall that is made of a resin material and partitions the accommodation spaces from each other. Accordingly, the sensor can be made lighter than that in the case where the separator is formed of a ceramic material, and the partition wall serves to reduce the risk that the strength of the separator will be reduced.

(2) In the sensor according to the above-described aspect, the base may be made of a resin material and the base may include a bottom portion at the back side in the axial direction and a side portion that extends from a peripheral edge of the bottom portion toward the front side in the axial direction so as to surround a radial periphery of the separator. The partition wall and the side portion may be connected directly or indirectly with a component other than the base provided therebetween.

According to the sensor of this aspect, since the partition wall and the side portion of the base are connected, the strength of the partition wall can be increased. Therefore, the risk that the strength of the separator will be reduced can be further reduced.

(3) In the sensor according to the above-described aspect, the base and the separator may be integrally formed of the resin material.

According to the sensor of this aspect, the base and the separator can be easily formed.

(4) In the sensor according to the above-described aspect, the partition wall may have a thickness that is constant in cross section orthogonal to the axial direction.

According to the sensor of this aspect, when the separator is made of a resin material, the risk of uneven thermal contraction of the separator can be reduced. As a result, the separator can be accurately manufactured.

(5) The sensor according to the above-described aspect may further include connector terminals for transmitting a detection signal output from the detector element to outside. The base may include a connector portion that extends in a direction crossing the axial direction and that accommodates one end portion of each connector terminal, and the other end portion of each connector terminal may be electrically connected to a corresponding one of the connection terminals in a corresponding one of the accommodation spaces.

According to the sensor of this aspect, since the connector portion extends in a direction crossing the axial direction, an increase in the size of the sensor in the axial direction can be suppressed.

(6) In the sensor according to the above-described aspect, the other end portion of each connector terminal may include a connector-terminal engagement portion having a recess or a hole, and each connection terminal may include a connection-terminal engagement portion that is inserted into the recess or the hole so as to be engaged with the connector-terminal engagement portion.

According to the sensor of this aspect, the connection-terminal engagement portion and the connector-terminal engagement portion engage with each other so that the electrical connection between the other end portion of each connector terminal and the corresponding connection terminal can be reliably maintained.

(7) In the sensor according to the above-described aspect, the connector terminals may be embedded in the base so that the connector terminals and the base are bonded together.

According to the sensor of this aspect, the connector terminals can be easily connected to the base.

The present invention can be embodied in various forms. For example, the present invention may be embodied not only as the sensor but also as a separator that accommodates connection terminals and a detector element, a method for manufacturing the separator, or a method for manufacturing the sensor.

BRIEF DESCRIPTION OF DRAWINGS

FIG. 12 illustrates a second connection terminal according to another embodiment.

DETAIL DESCRIPTION OF EXEMPLARY EMBODIMENTS OF THE INVENTION

A. Embodiment

Figure 1:
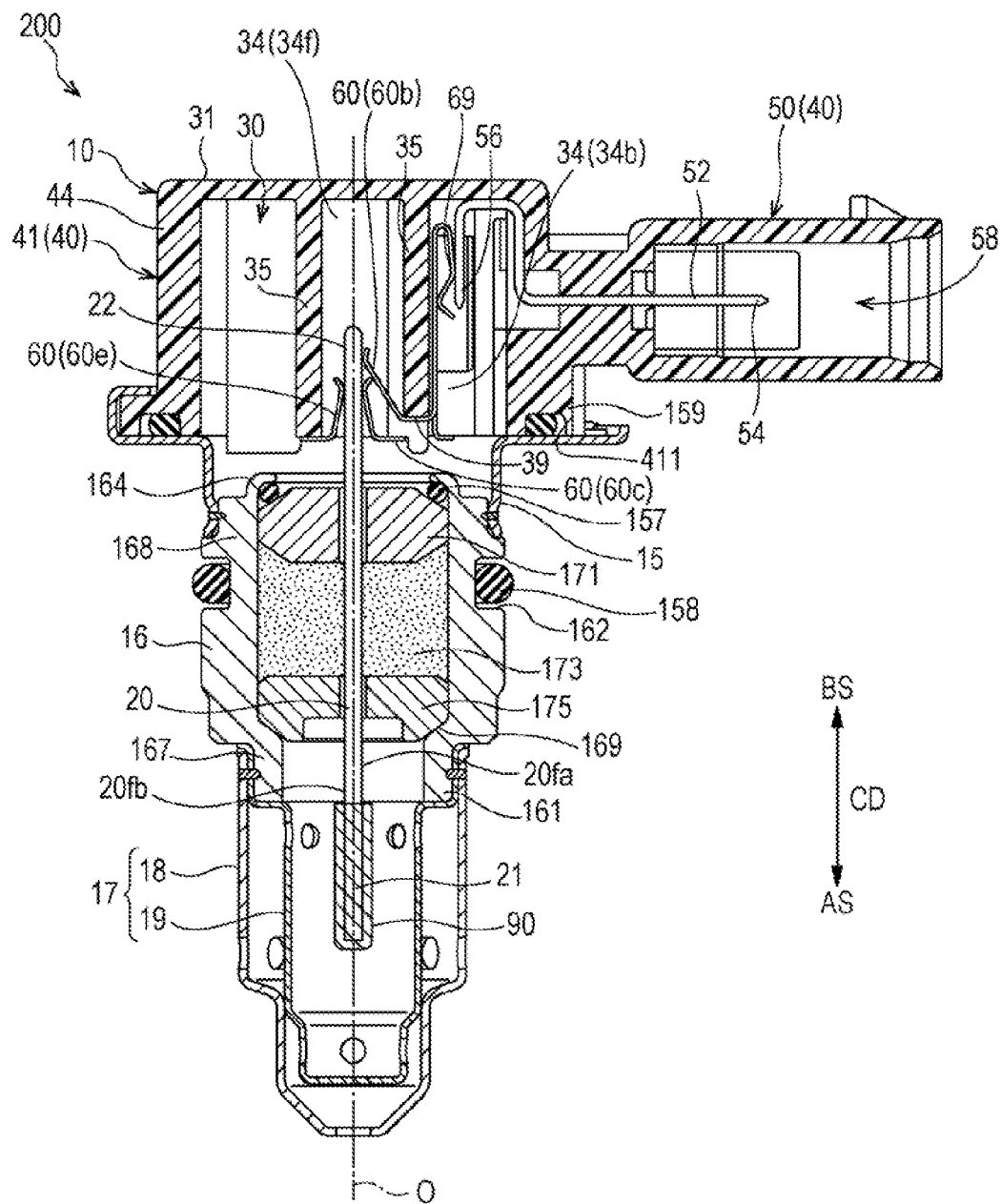
FIG. 1 is a sectional view of a sensor according to an embodiment of the present invention.
Figure 2:
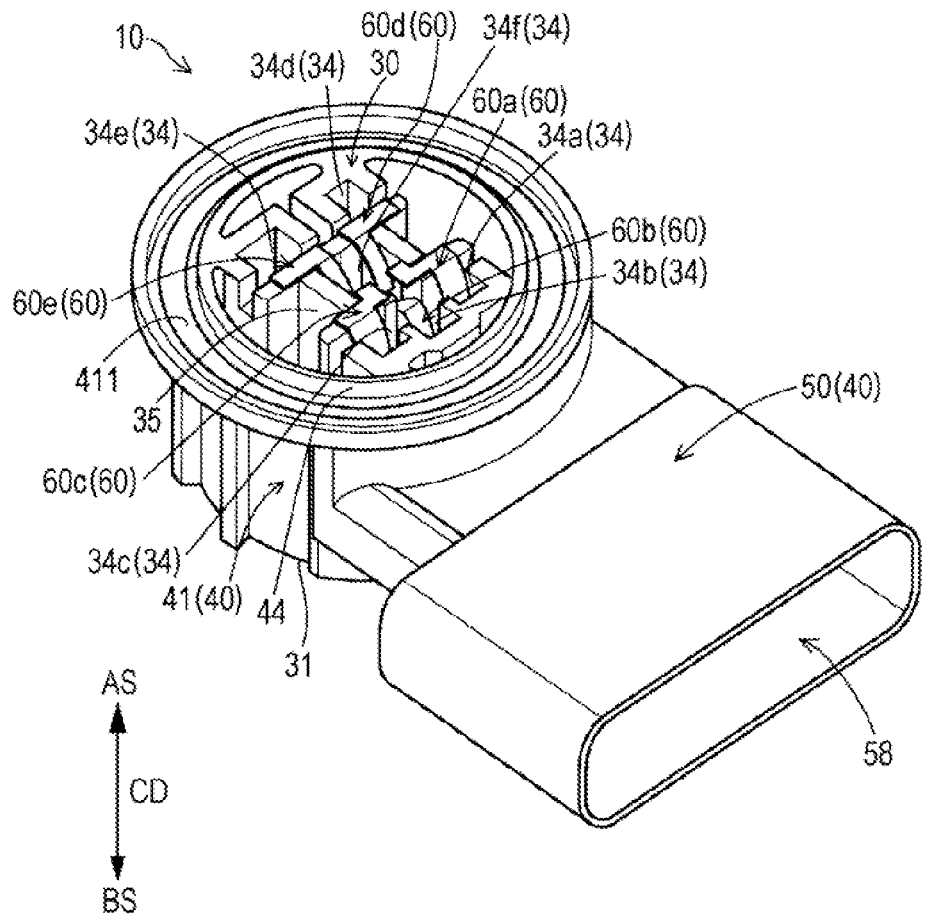
FIG. 2 is a perspective view of a terminal accommodation unit.
Figure 3:
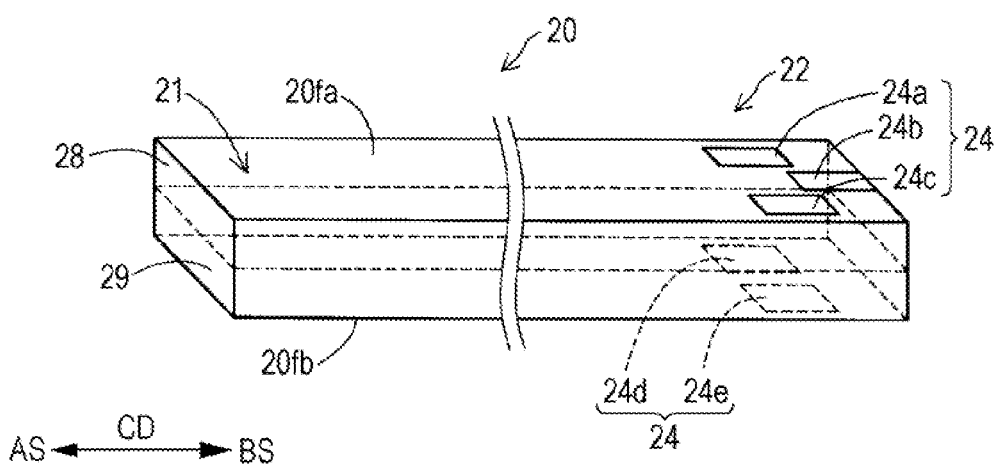
FIG. 3 is a perspective view of a detector element.

FIG. 1 is a sectional view of a sensor 200 according to an embodiment of the present invention. FIG. 2 is a perspective view of a terminal accommodation unit 10. FIG. 3 is a perspective view of a detector element 20. In FIG. 1, a direction parallel to an axis O of the detector element 20 is defined as an axial direction CD, the upper side of FIG. 1 is defined as a back side BS of the sensor 200, and the lower side of FIG. 1 is defined as a front side AS of the sensor 200. The sensor 200 is attached to, for example, an inlet system of an internal combustion engine, and outputs a detection signal for detecting an oxygen concentration in measurement target gas that flows through the inlet system.

The sensor 200 (FIG. 1) includes the terminal accommodation unit 10, an attachment 15, a metal shell 16, and a protector 17, which are arranged in that order from the back side BS to the front side AS. The sensor 200 also includes the detector element 20 that extends in the axial direction CD.

The detector element 20 is plate shaped, and has a first plate surface 20fa and a second plate surface 20fb that extend in the axial direction CD and oppose each other. The first plate surface 20fa and the second plate surface 20fb serve as principal surfaces of the detector element 20, and have the largest area in the outer surface of the detector element 20. As illustrated in FIG. 3, the detector element 20 includes a detecting portion 21 at the front side AS in the axial direction CD and an element back portion 22 at the back side BS in the axial direction CD. The element back portion 22 includes first to third metal terminal portions 24a to 24c formed on the first plate surface 20fa and fourth and fifth metal terminal portions 24d and 24e formed on the second plate surface 20fb. Each of the metal terminal portions 24a to 24e is made of a metal, such as platinum, or a conductive material and has a substantially rectangular surface. The second metal terminal portion 24b is located further toward the back side BS than the other metal terminal portions 24a, 24c, 24d, and 24e. The first to fifth metal terminal portions 24a to 24e are referred to as "metal terminal portions 24" when it is not necessary to distinguish them from each other. The metal terminal portions 24 correspond to "electrical connection terminal portions" described in the Summary of the Invention section. The detecting portion 21 is used to detect the concentration of a specific gas component (for example, oxygen) in the measurement target gas. As illustrated in FIG. 1, the front section of the detector element 20 in which the detecting portion 21 is provided is covered with a detecting-portion protecting layer 90 formed of a porous material.

The detector element 20 (FIG. 3) is used as an air-fuel ratio sensor, and has a structure similar to that of a detector element of the related art. Therefore, detailed description of the inner structure, for example, of the detector element 20 will be omitted, and the rough structure will be described. The detector element 20 has a multilayer body obtained by stacking a plate-shaped element layer 28, on which the detecting portion 21 is formed, and a plate-shaped heater layer 29 for heating the element layer 28. The element layer 28 is formed by stacking assemblies, which each include a solid electrolyte body containing zirconia as the main component and a pair of electrodes containing platinum as the main component, with an insulating layer interposed therebetween, the insulating layer having a hollow measurement chamber formed in a portion thereof. The element layer 28 includes an oxygen pump cell configured such that one of the pair of electrodes formed on both surfaces of the solid electrolyte body (hereinafter referred to as "first electrode") is externally exposed and the other of the pair of electrodes (hereinafter referred to as "second electrode") is disposed in the measurement chamber, and an oxygen concentration measurement cell configured such that one of the pair of electrodes formed on both surfaces of the solid electrolyte body is disposed in the measurement chamber and the other of the pair of electrode is disposed in a reference gas chamber. The element layer 28 controls a current that flows between the pair of electrodes of the pump cell so that an output voltage of the oxygen concentration measurement cell is a predetermined value, thereby discharging oxygen from the measurement chamber or introducing oxygen into the measurement chamber from the outside. The pair of electrodes and a portion of the solid electrolyte body sandwiched by the electrodes in the oxygen pump cell form the detecting portion 21 through which a current corresponding to the oxygen concentration flows. The metal terminal portions 24 are used to transmit the detection signal from the detecting portion 21 and supplying electric power to heating wires embedded in the heater layer 29.

The terminal accommodation unit 10 (FIG. 1) includes a separator 30, which has a cylindrical shape with a bottom and includes a bottom portion 31 at the back side BS, and a base 40, which also has a cylindrical shape with a bottom. The bottom portion 31 also serves as a bottom portion of the base 40. In other words, the separator 30 and the base 40 have a common bottom portion. The base 40 includes a cylindrical main body 41 that surrounds the outer periphery of the separator 30 and a connector portion 50 that extends from the main body 41 in a direction that crosses the axial direction CD. In the present embodiment, the connector portion 50 extends in a direction orthogonal to the axial direction CD. The terminal accommodation unit 10 is integrally formed of a resin material (integrally molded). The resin material may be a highly formable resin, such as nylon (registered trademark), polyamide (PA), polybutylene terephthalate (PBT), or polyphenylene sulfide (PPS).

The separator 30 (FIG. 2) includes first to sixth accommodation spaces 34a to 34f that receive the detector element 20 and connection terminals 60, which will be described below, and a partition wall 35 that partitions the six accommodation spaces 34a to 34f from each other. As illustrated in FIG. 1, the partition wall 35 includes a plurality of plate-shaped members that extend from the bottom portion 31 to the front end surface of the separator 30. The partition wall 35 partitions the first to sixth accommodation spaces 34a to 34f in a plane orthogonal to the axial direction CD. As illustrated in FIG. 2, each of the first to fifth accommodation spaces 34a to 34e accommodates a corresponding one of first to fifth connection terminals 60a to 60e (more specifically, frame main bodies of the first to fifth connection terminals 60a to 60e, which will be described below). The sixth accommodation space 34f accommodates the element back portion 22 of the detector element 20 and portions of the first to fifth connection terminals 60a to 60e (more specifically, portions of element contact portions of the first to fifth connection terminals 60a to 60e, which will be described below).

As illustrated in FIG. 2, when the separator 30 is viewed from the front side AS, the sixth accommodation space 34f is located in a substantially central region of the cylindrical separator 30, and the first to fifth accommodation spaces 34a to 34e are located further toward the outer side in the radial direction of the separator 30 than the sixth accommodation space 34f. The first to sixth accommodation spaces 34a to 34f are referred to as "accommodation spaces 34" when it is not necessary to distinguish them from each other. The first to fifth connection terminals 60a to 60e are referred to as "connection terminals 60" when it is not necessary to distinguish them from each other. The detailed structure of the separator 30 will be described below. The first to fifth accommodation spaces 34a to 34e correspond to the "terminal accommodation spaces" described in the Summary of the Invention section, and the sixth accommodation space 34f corresponds to the "element accommodation space" described in the Summary of the Invention section.

The main body 41 of the base 40 includes a side portion 44 that surrounds the outer periphery of the separator 30. The side portion 44 extends from the peripheral edge of the bottom portion 31 at the back side BS in the axial direction CD toward the front side AS in the axial direction CD. The side portion 44 is arranged so as to surround the periphery of the separator 30 in the radial direction. As illustrated in FIG. 1, the partition wall 35 and the side portion 44 are indirectly connected to each other by the bottom portion 31. In addition, as illustrated in FIG. 2, the partition wall 35 and the side portion 44 are directly connected to each other at least at the front side AS. The state in which the partition wall 35 and the side portion 44 are "directly connected" means that they are attached to each other without any component interposed therebetween. The state in which the partition wall 35 and the side portion 44 are "indirectly connected" means that they are attached to each other with another component interposed therebetween. The front end surface of the main body 41 has a groove 411 that extends in the circumferential direction. The detailed structure of the main body 41 will be described below.

The connector portion 50 (FIG. 1) accommodates connector terminals 52 (more specifically, one end portion 54 of each connector terminal 52) for transmitting the detection signal output from the detector element 20 to the outside. Five connector terminals 52 are provided (only one of them is shown in FIG. 1) so that the number of connector terminals 52 corresponds to the number of connection terminals 60. The connector terminals 52 are bonded to the base 40 such that the connector terminals 52 are embedded in the base 40 by being insert-molded in the base 40. In other words, a resin that forms the base 40 and the connector terminals 52 are subjected to resin molding. More specifically, the connector terminals 52 are disposed in a mold, and the resin is injected into the space around the connector terminals 52, so that the connector terminals 52 are attached to the base 40. The connector terminals 52 can be easily fixed to the base 40 by insert molding.

The other end portion 56 of each connector terminal 52 is electrically connected to a corresponding one of the connection terminals 60 in a corresponding one of the first to fifth accommodation spaces 34a to 34e. The one end portion 54 of each connector terminal 52 is disposed in an opening 58 in the connector portion 50. When an external connector is inserted into the opening 58, the one end portion 54 of each connector terminal 52 is connected to the corresponding terminal included in the external connector. Thus, the detection signal is transmitted through the external connector to a detection device that calculates the oxygen concentration.

The metal shell 16 is a cylindrical component in which the detector element 20 is disposed. The metal shell 16 is made of a stainless steel, such as SUS430. The metal shell 16 surrounds the detector element 20 with the axis of the detector element 20 in the axial direction CD at the center. The metal shell 16 holds the detector element 20 such that the detecting portion 21 of the detector element 20 projects therefrom at the front side AS and the element back portion 22 of the detector element 20 projects therefrom at the back side BS. The metal shell 16 includes a back-side outer peripheral portion 168 at the back side BS thereof, and the attachment 15 is attached to the back-side outer peripheral portion 168 by laser welding or the like. The metal shell 16 includes a front-side outer peripheral portion 167 at the front side AS thereof, and the protector 17 is attached to the front-side outer peripheral portion 167 by laser welding.

The metal shell 16 further includes a groove portion 162 that is located between the back-side outer peripheral portion 168 and the front-side outer peripheral portion 167 in the axial direction CD and that extends over the entire circumference. A sealing member 158 is disposed in the groove portion 162. In the present embodiment, the sealing member 158 is an O-ring. The sealing member 158 seals the space between the sensor 200 and an object to which the sensor 200 is attached. More specifically, when the sensor 200 is attached to the object, the sealing member 158 is deformed by being pressed against an inner wall of a sensor attachment hole, thereby sealing the space between the sensor attachment hole and the sensor 200.

A cylindrical ceramic holder 175 made of alumina, a powder-filled layer 173 made of talcum powder, and a cylindrical ceramic sleeve 171 made of alumina are arranged in that order from the front side AS to the back side BS in the metal shell 16. A crimping ring 157 is disposed between the ceramic sleeve 171 and a back end portion 164 of the metal shell 16.

The ceramic holder 175 is retained by a ledge portion 169 located at the front side AS of the metal shell 16. The ceramic sleeve 171 and the ceramic holder 175 are cylindrical components having rectangular shaft holes that extend in the axial direction CD. The plate-shaped detector element 20 is supported by being inserted through the rectangular shaft holes in the ceramic sleeve 171 and the ceramic holder 175 in the axial direction CD. After the ceramic sleeve 171 is disposed in the metal shell 16, the back end portion 164 of the metal shell 16 is bent radially inward and crimped toward the back end surface of the ceramic sleeve 171 with the crimping ring 157 interposed therebetween. Thus, the ceramic sleeve 171 is fixed to the metal shell 16.

The protector 17 (FIG. 1) includes an outer protector 18 and an inner protector 19 disposed in the outer protector 18. The outer protector 18 and the inner protector 19 have a cylindrical shape with a bottom. Each of the outer protector 18 and the inner protector 19 is a metal member having a plurality of holes. The measurement target gas flows into the inner protector 19 through the holes. The outer protector 18 and the inner protector 19 cover the detecting portion 21 of the detector element 20 to protect the detecting portion 21 from external water or the like.

The attachment 15 is a member that connects the metal shell 16 and the terminal accommodation unit 10. The attachment 15 is a component made of a metal, such as stainless steel. A portion of the attachment 15 at the front side AS is attached to the metal shell 16 by laser welding or the like, and a portion of the attachment 15 at the back side BS is attached to the base 40 of the terminal accommodation unit 10 by crimping or the like. A sealing member 159 is disposed in the groove 411 formed in the front end surface of the base 40 (more specifically, the main body 41). The sealing member 159 is an O-ring. The sealing member 159 seals between attachment portions of the attachment 15 and the base 40. The attachment 15 has a pair of flange portions (not shown) that project in the direction of the plane of FIG. 1. The flange portions have holes. Screws are inserted through the holes and screwed into threaded holes formed in the object to which the sensor 200 is to be attached. Thus, the sensor 200 is attached to the object. The number of threaded holes may instead be one.

Figure 4:
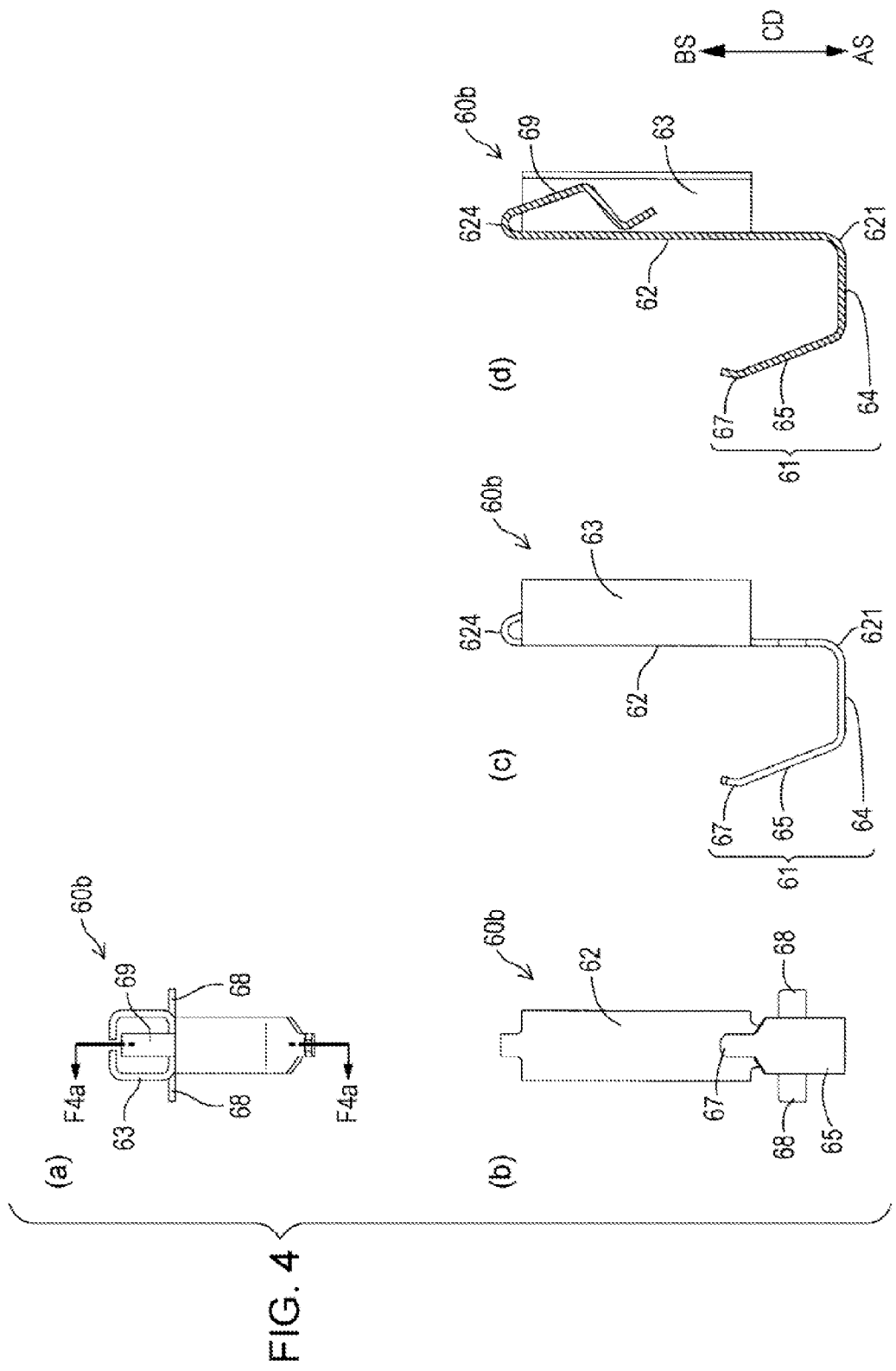
FIG. 4 illustrates a second connection terminal.

FIG. 4 illustrates the second connection terminal 60b. FIG. 4(a) is a top view of the second connection terminal 60b. FIG. 4(b) is a front view of the second connection terminal 60b. FIG. 4(c) is a right side view of the second connection terminal 60b. FIG. 4(d) is a sectional view taken along line F4a-F4a in FIG. 4(a). FIG. 4(d) shows the axial direction CD in the state in which the second connection terminal 60b is attached to the sensor 200.

As illustrated in FIG. 4(d), the second connection terminal 60b includes a connector contact portion 69, a frame main body 62, an element contact portion 61, a protruding portion 63, and two retaining portions 68 (FIG. 4(b)). As illustrated in FIG. 4(b), the frame main body 62 is oblong-plate-shaped and extends in the axial direction CD.

The element contact portion 61 is bent at a front end portion 621 of the frame main body 62 and extends toward the back side BS. The element contact portion 61 includes an inner extending portion 64 that extends from the front end portion 621 of the frame main body 62 toward the detector element 20 (so as to approach the detector element 20), and a spring portion 65 that is connected to the detector-device-20-side end of the inner extending portion 64 and extends toward the back side BS. The inner extending portion 64 according to the present embodiment extends linearly in the horizontal direction. The spring portion 65 extends toward the back side BS and the detector element 20. The spring portion 65 has an element contact portion 67 at the back side BS thereof. The element contact portion 67 comes into contact with the corresponding metal terminal portion 24 so as to be electrically connected to the metal terminal portion 24.

The connector contact portion 69 is bent at a back end portion 624 of the frame main body 62 and extends toward the front side AS. The connector contact portion 69 is bent on a side of the frame main body 62 opposite to the side at which the element contact portion 61 is located. As illustrated in FIGS. 4(a) and 4(d), the protruding portion 63 extends from the frame main body 62 on the side opposite to the side at which the element contact portion 61 is located. The protruding portion 63 is formed so as to surround the connector contact portion 69. The protruding portion 63 is disposed in the second accommodation space 34b, and comes into contact with a wall surface of the second accommodation space 34b so that the movement of the second connection terminal 60b is restrained. As illustrated in FIG. 4(b), the two retaining portions 68 are plate-shaped portions that extend in the width direction of the frame main body 62 at the front side AS of the frame main body 62. The two retaining portions 68 are placed in grooves formed in the front end surface of the separator 30 and retained by the separator 30, so that deformation of the frame main body 62 toward the detector element 20 is suppressed.

Figure 5:
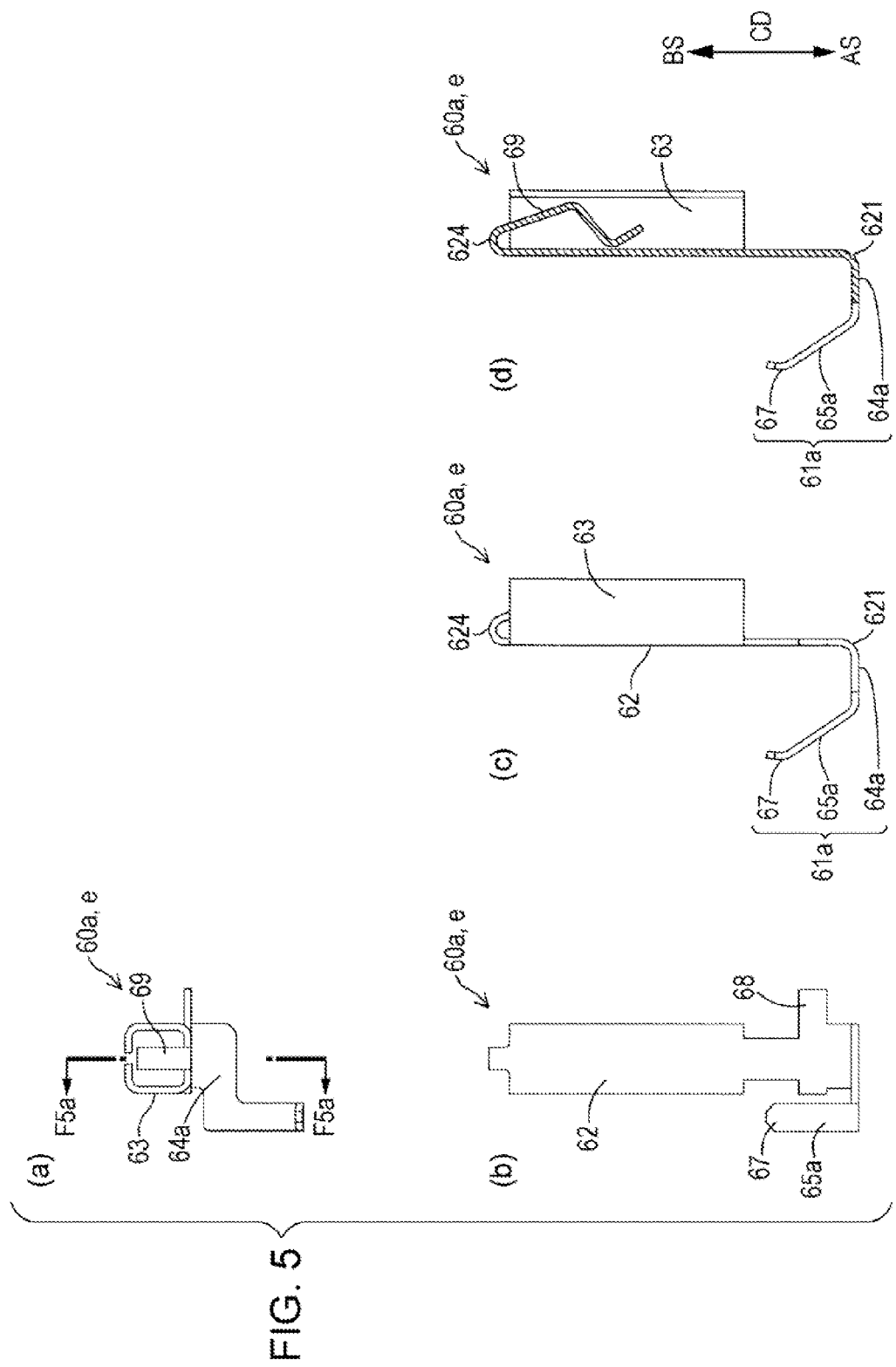
FIG. 5 illustrates third and fourth connection terminals.

FIG. 5 illustrates the first and fifth connection terminals 60a and 60e. FIG. 5(a) is a top view of the first and fifth connection terminals 60a and 60e. FIG. 5(b) is a front view of the first and fifth connection terminals 60a and 60e. FIG. 5(c) is a right side view of the first and fifth connection terminals 60a and 60e. FIG. 5(d) is a sectional view taken along line F5a-F5a in FIG. 5(a). FIG. 5(d) shows the axial direction CD in the state in which the first and fifth connection terminals 60a and 60e are attached to the sensor 200. The difference between the first and fifth connection terminals 60a and 60e and the second connection terminal 60b (FIG. 4) is the number of retaining portions 68 and the structure of an element contact portion 61a. The structures of other portions of the first and fifth connection terminals 60a and 60e are similar to those of the second connection terminal 60b. Therefore, similar portions are denoted by the same reference numerals and description thereof is omitted.

The number of retaining portions 68 is one (FIG. 5(b)). The retaining portion 68 projects in the width direction of a frame main body 62 at the front side AS of the frame main body 62. As illustrated in FIG. 5(c), the element contact portion 61a is bent at a front end portion 621 of the frame main body 62 and extends toward the back side BS. The element contact portion 61a differs from the element contact portion 61 of the second connection terminal 60b (FIG. 4) in that an inner extending portion 64a has a bent portion that is bent in the width direction of the frame main body 62 and the width of a spring portion 65a is smaller than that of the spring portion 65 (FIG. 4). As illustrated in FIGS. 5(a) and 5(b), the inner extending portion 64a extends linearly in the horizontal direction, and is bent in the width direction of the frame main body 62 on the side at which the inner extending portion 64a is connected to the spring portion 65a. Here, the bending direction is opposite to the direction in which the retaining portion 68 projects.

The third and fourth connection terminals 60c and 60d (FIG. 2) differ from the first and fifth connection terminals 60a and 60e only in that the positions of the retaining portion 68 and the element contact portion 61a with respect to the frame main body 62 are opposite to those in the first and fifth connection terminals 60a and 60e. In other words, referring to FIG. 5(b), in the third and fourth connection terminals 60c and 60d, the retaining portion 68 is on the left side of the frame main body 62 and the spring portion 65a is on the right side of the frame main body 62.

Figure 6:
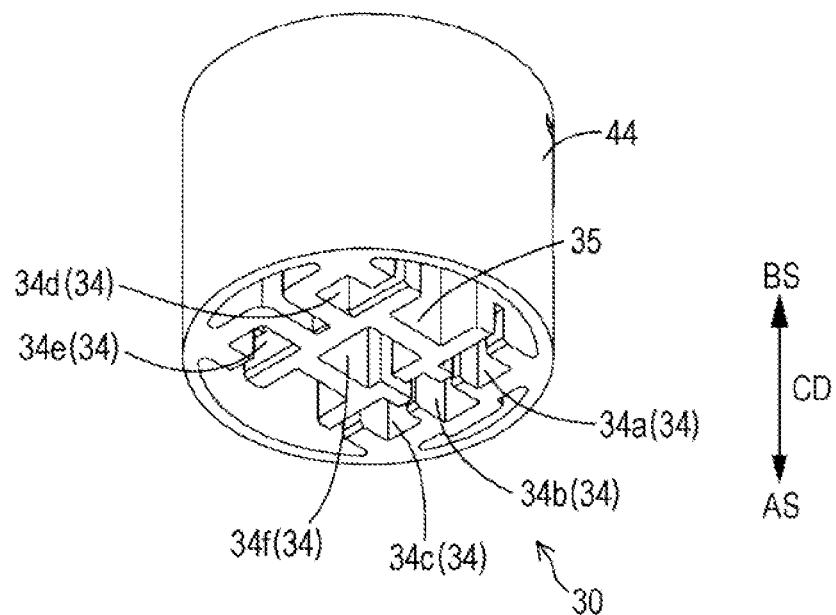
FIG. 6 is a perspective view of a separator and a side portion of a base.
Figure 7:
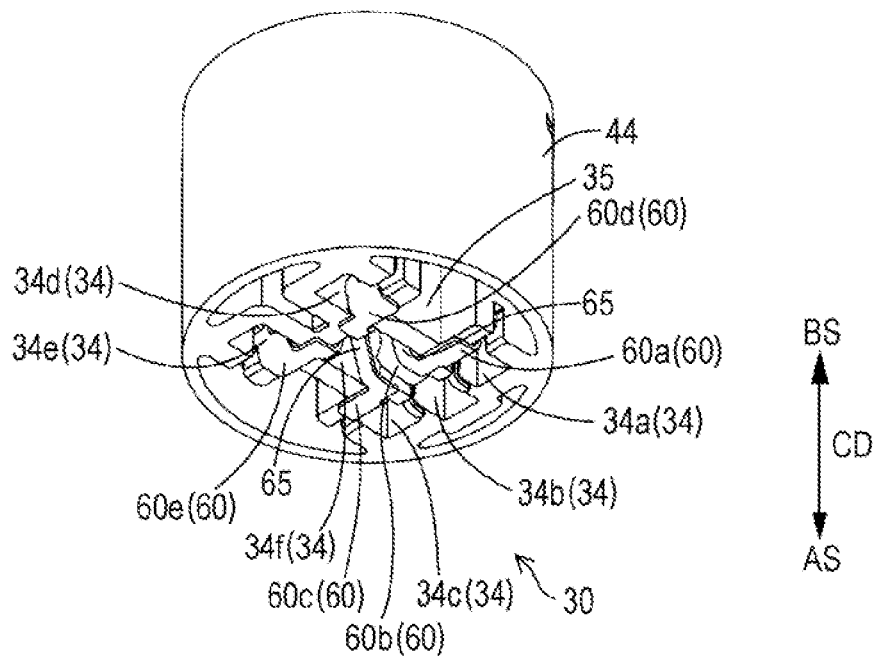
FIG. 7 is a perspective view illustrating the state in which connection terminals are attached to the separator.
Figure 8:
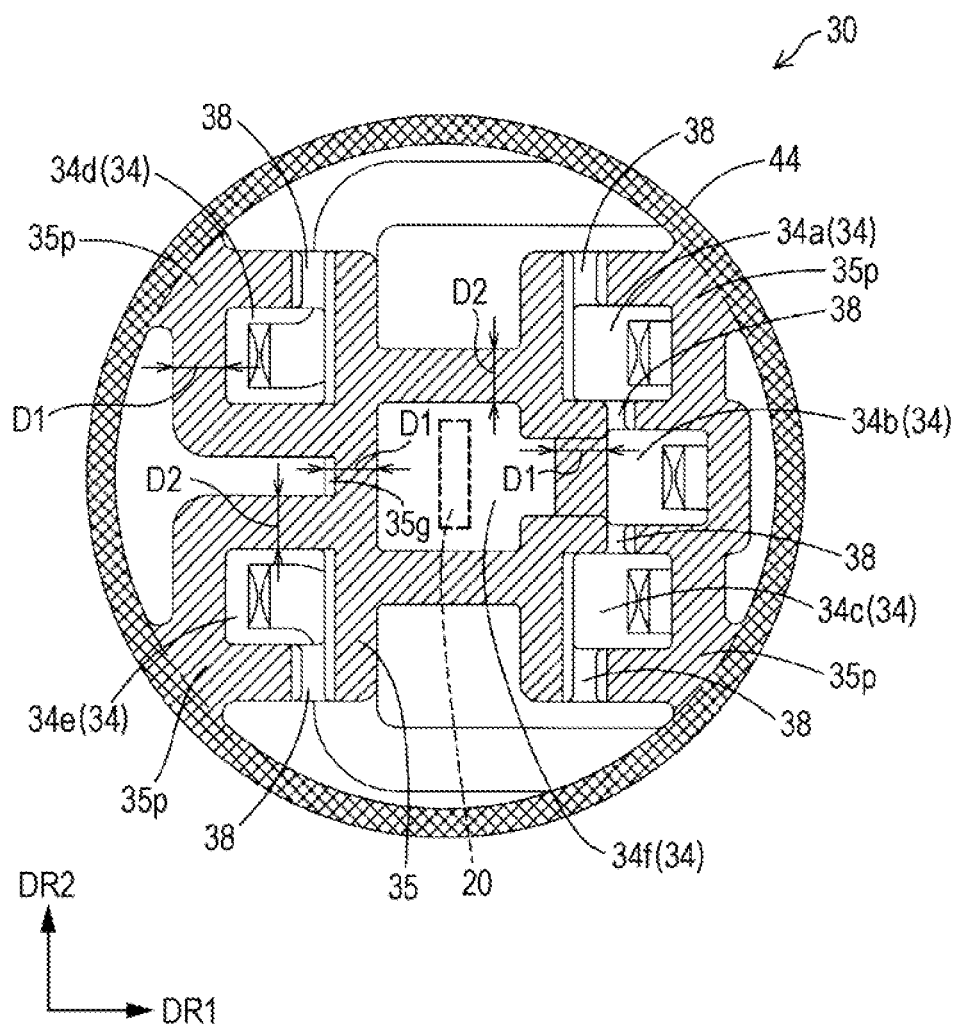
FIG. 8 illustrates the structure shown in FIG. 6 viewed from a front side.
Figure 9:
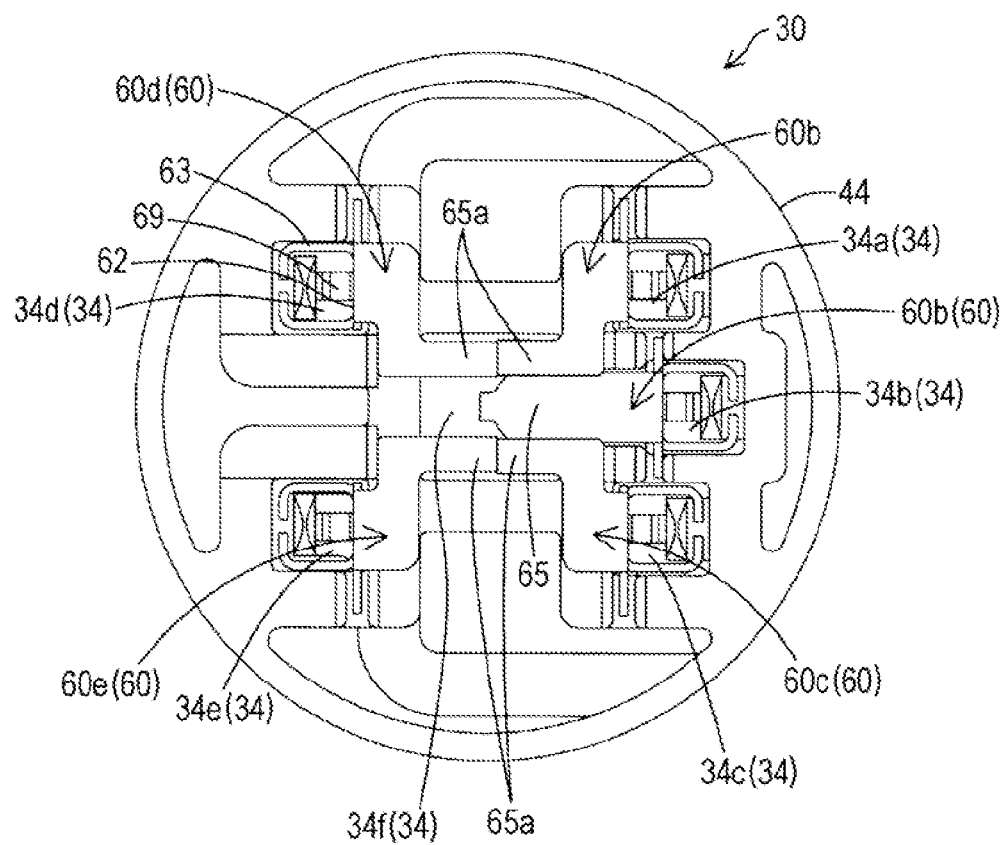
FIG. 9 illustrates the structure shown in FIG. 7 viewed from the front side.

FIG. 6 is a perspective view of the separator 30 and the side portion 44 of the base 40. FIG. 7 is a perspective view illustrating the state in which the connection terminals 60 are attached to the separator 30. FIG. 8 illustrates the structure shown in FIG. 6 viewed from the front side AS. FIG. 9 illustrates the structure shown in FIG. 7 viewed from the front side AS. FIGS. 6 and 7 illustrate a portion of the side portion 44 (FIG. 2) on the inner side of the groove 41l in the radial direction. In FIG. 8, to facilitate understanding, the front end surface of the side portion 44 is shown as the cross-hatched area, the front end surface of the partition wall 35 is shown as the single-hatched area, and the location at which the detector element 20 is disposed is shown by the dashed line.

As illustrated in FIGS. 6 and 7, the partition wall 35 of the separator 30 partitions the accommodation spaces 34 from each other. More specifically, the accommodation spaces 34 are partitioned by the partition wall 35 such that each accommodation space 34 has a substantially rectangular cross section along a plane orthogonal to the axial direction CD. In other words, the partition wall 35 forms side walls of the accommodation spaces 34 that extend in the axial direction CD. Accordingly, when the connection terminals 60 and the detector element 20 are disposed in the separator 30, portions of the frame main bodies 62 of the connection terminals 60 and the detector element 20 around the axes thereof in the axial direction CD are surrounded by the partition wall 35. As illustrated in FIG. 8, the front end surface of the partition wall 35 is directly connected to the side portion 44. More specifically, four corner portions 35p of the front end surface of the partition wall 35 on the radially outer side of the separator 30 are connected to the side portion 44. In addition, the partition wall 35 is indirectly connected to the side portion 44 by the bottom portion 31 of the base 40 (FIG. 1). The front end surface of the partition wall 35 has grooves 38 that receive the retaining portions 68 of the connection terminals 60 (FIGS. 4(b) and 5(b)).

As illustrated in FIG. 9, each of the first to fifth accommodation spaces 34a to 34e accommodates the frame main body 62, the protruding portion 63, and the connector contact portion 69 of the corresponding connection terminal 60. The sixth accommodation space 34f accommodates the element back portion 22 of the detector element 20 (FIG. 1) and the spring portions 65 and 65a of the connection terminals 60. The partition wall 35 preferably has constant thicknesses D1 and D2 (FIG. 8) in cross section orthogonal to the axial direction CD. In such a case, when the separator 30 is formed by injection molding or the like by using a resin material, the risk of uneven thermal contraction of the separator 30 can be reduced. Accordingly, the separator 30 can be accurately manufactured. The front end surface of the partition wall 35 is partially chamfered so that a chamfered portion 35g is formed. In other embodiments, the partition wall 35 is not required to have constant thicknesses.

The thicknesses D1 and D2 of the partition wall 35 are thicknesses in the following first and second directions that are orthogonal to the axial direction CD.

First Direction DR1: Direction that is orthogonal to the axial direction CD and in which the first plate surface 20fa and the second plate surface 20fb of the detector element 20 face each other.

Second Direction DR2: Direction orthogonal to the axial direction CD and the first direction DR1.

In the present embodiment, the thickness of the partition wall 35 in the first direction DR1 is defined as the thickness D1, and the thickness of the partition wall 35 in the second direction DR2 is defined as the thickness D2.

In the above-described embodiment, the separator 30 is formed of a resin material, and the partition wall of the separator 30 that partitions the accommodation spaces 34 is integrally formed. Accordingly, the sensor can be made lighter than that in the case where the separator 30 is formed of a ceramic material, and the partition wall 35 serves to reduce the risk that the strength of the separator 30 will be reduced. In the above-described embodiment, as illustrated in FIG. 8, the partition wall 35 is directly connected to the side portion 44 of the base 40 at the corner portions 35p. In addition, as illustrated in FIG. 1, the partition wall 35 and the side portion 44 are indirectly connected to each other by the bottom portion 31. Accordingly, the strength of the partition wall 35 can be increased, so that the risk that the strength of the separator 30 will be reduced can be further reduced. In addition, in the above-described embodiment, the base 40 including the side portion 44 and the separator 30 are integrally formed of a resin material. Thus, the base 40 and the separator 30 can be easily formed. In the above-described embodiment, as illustrated in FIG. 1, each connector terminal 52 extends in a direction orthogonal to the axial direction CD (orthogonal direction), and the base 40 includes the connector portion 50 that extends in the orthogonal direction. Thus, an increase in the size of the sensor 200 in the axial direction CD can be suppressed.

B. Other Connection Modes Between Separator and Side Portion

Figure 10:
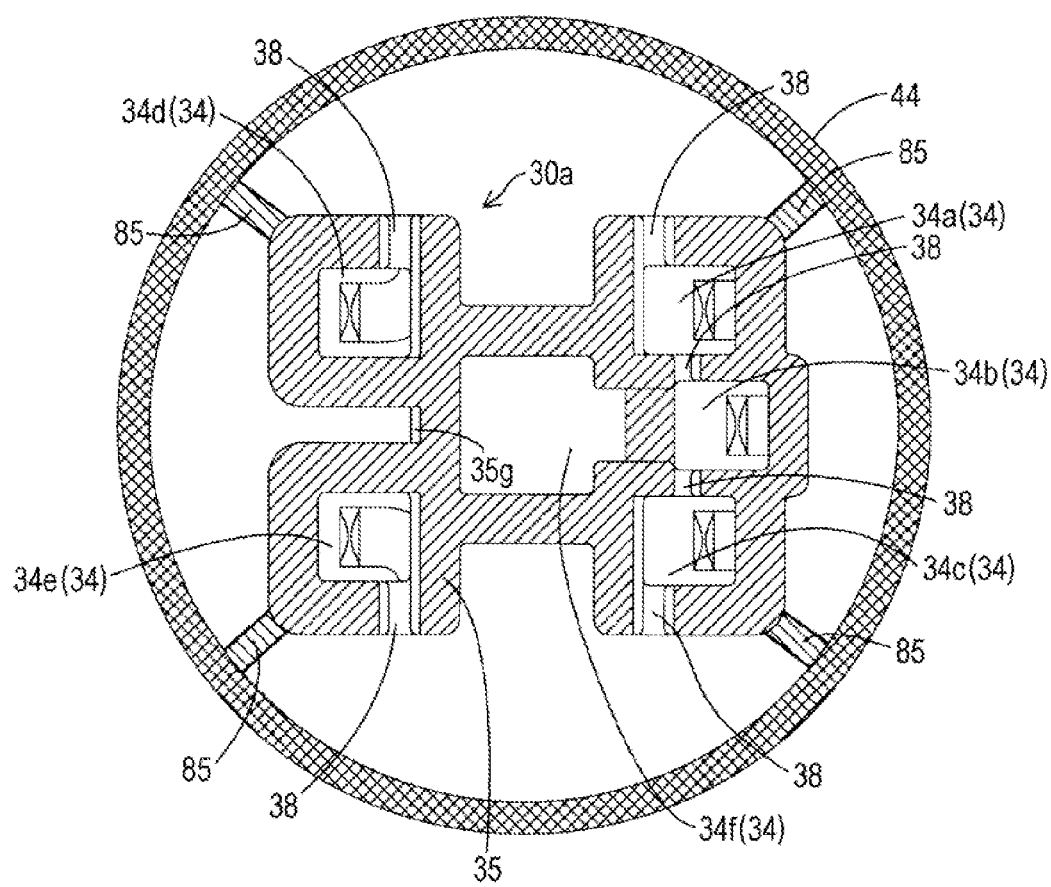
FIG. 10 illustrates a first mode of connection between the separator and the side portion.
Figure 11:
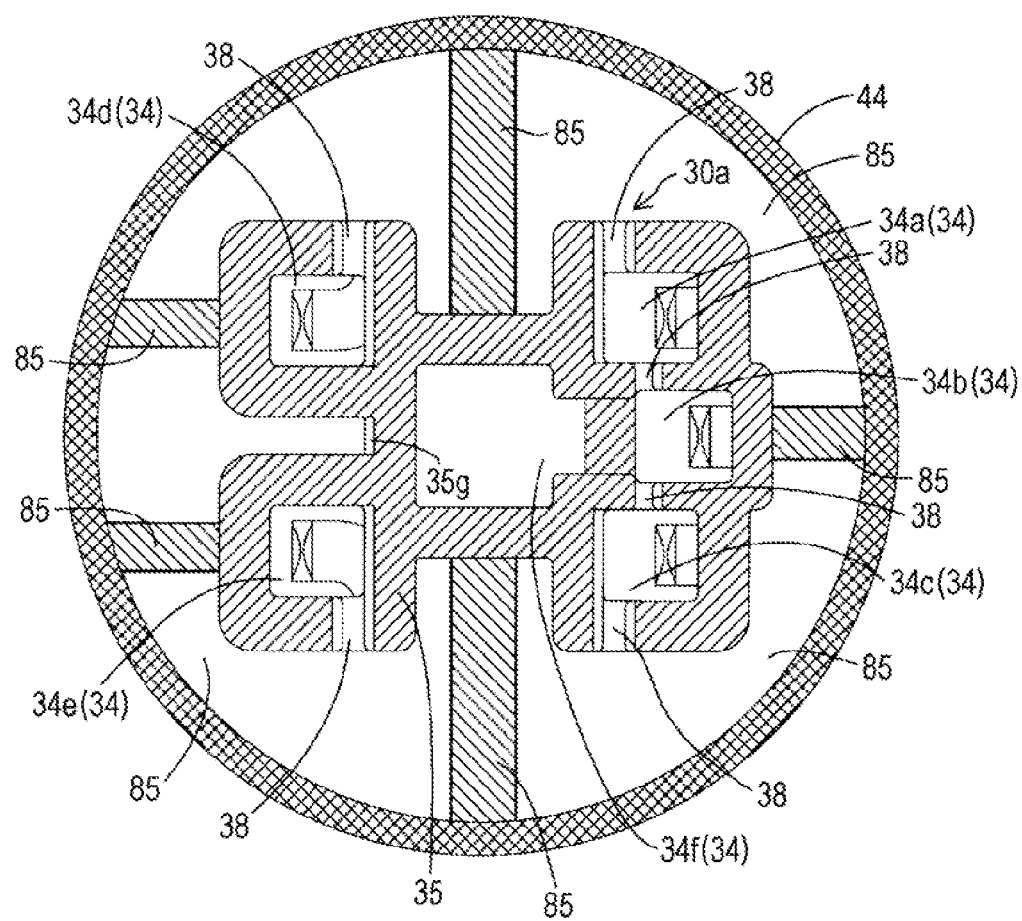
FIG. 11 illustrates a second mode of connection between the separator and the side portion.

FIG. 10 illustrates a first mode of connection between the separator 30 and the side portion 44. FIG. 11 illustrates a second mode of connection between the separator 30 and the side portion 44. FIGS. 10 and 11 are diagrams corresponding to FIG. 8 of the above-described embodiment. Although the partition wall 35 and the side portion 44 of the base 40 are directly connected at the corner portions 35p in the above-described embodiment, they may instead be indirectly connected with another component interposed therebetween. In FIGS. 10 and 11, the separator 30 and the side portion 44 of the base 40 are connected by other components, which are connecting members 85. The connecting members 85 are ribs that project radially inward from an inner peripheral surface of the side portion 44. The connecting members 85 extend in the axial direction CD from the bottom portion 31 (FIG. 1) to the front end surface of the partition wall 35. The connecting members 85 may be made of the same resin material as the material of the separator 30. Alternatively, the connecting members 85 may be formed of a metal, such as stainless steel, or a resin material different from the material of the separator 30. Since the connecting members 85 are attached to the side portion 44 and the partition wall 35, the side portion 44 and the partition wall 35 are indirectly connected. The partition wall 35 and the side portion 44 may instead be connected by being attached together with an adhesive or filler that serves as another component instead of the connecting members 85. Also in this case, similar to the above-described embodiment, the strength of the partition wall 35 can be increased, so that the risk that the strength of the separator 30 will be reduced can be further reduced. Moreover, although the partition wall 35 and the side portion 44 are indirectly connected by the bottom portion 31 of the base 40 in the above-described embodiment as illustrated in FIG. 1, it is not necessary that they be connected by the bottom portion 31.

C. Other Embodiments of Connection Terminals and Connector Terminals

FIG. 12 illustrates a second connection terminal 60*ba* according to another embodiment. FIG. 12(*a*) is a top view of the second connection terminal 60*ba*. FIG. 12(*b*) is a front view of the second connection terminal 60*ba*. FIG. 12(*c*) is a right side view of the second connection terminal 60*ba*. The second connection terminal 60*ba* may be used as a component of the sensor 200 in place of the second connection terminal 60*b* (FIG. 4) of the above-described embodiment. The second connection terminal 60*ba* differs from the second connection terminal 60*b* of the above-described embodiment in that a protruding portion 63*a* has a mechanism that engages with the other end portion 56*a* of a connector terminal 52*a*, which will be described below. The structures of other portions of the second connection terminal 60*ba* are similar those of the second connection terminal 60*b*. Therefore, similar portions are denoted by the same reference numerals and description thereof is omitted.

The protruding portion 63*a* includes a pair of side portions 63A and 63B that are connected to end portions of the frame main body 62 in a width direction WD (left-right direction in FIG. 12(*b*)) and that cross the frame main body 62. One of the pair of side portions 63A and 63B is referred to as a first side portion 63A, and the other is referred to as a second side portion 63B. The first and second side portions 63A and 63B project on a side opposite to the side at which the element contact portion 61 is located. The first and second side portions 63A and 63B face each other in the width direction WD of the frame main body 62. The first and second side portions 63A and 63B are arranged such that the connector contact portion 69 is disposed therebetween.

As illustrated in FIGS. 12(*b*) and 12(*c*), the first and second side portions 63A and 63B each include a connection-terminal engagement portion 663 and a hole 661 that engage with the other end portion 56*a* of the connector terminal 52*a*, which will be described below, in the axial direction CD. The connection-terminal engagement portions 663 are located on the back side BS of the holes 661. The connection-terminal engagement portions 663 are plate-shaped and elastically deformable in the width direction WD. Although the first and second side portions 63A and 63B of the second connection terminal 60*ba* are described, the first and second side portions 63A and 63B are also formed on the other connection terminals (first, third, fourth, and fifth connection terminals).

Figure 13:
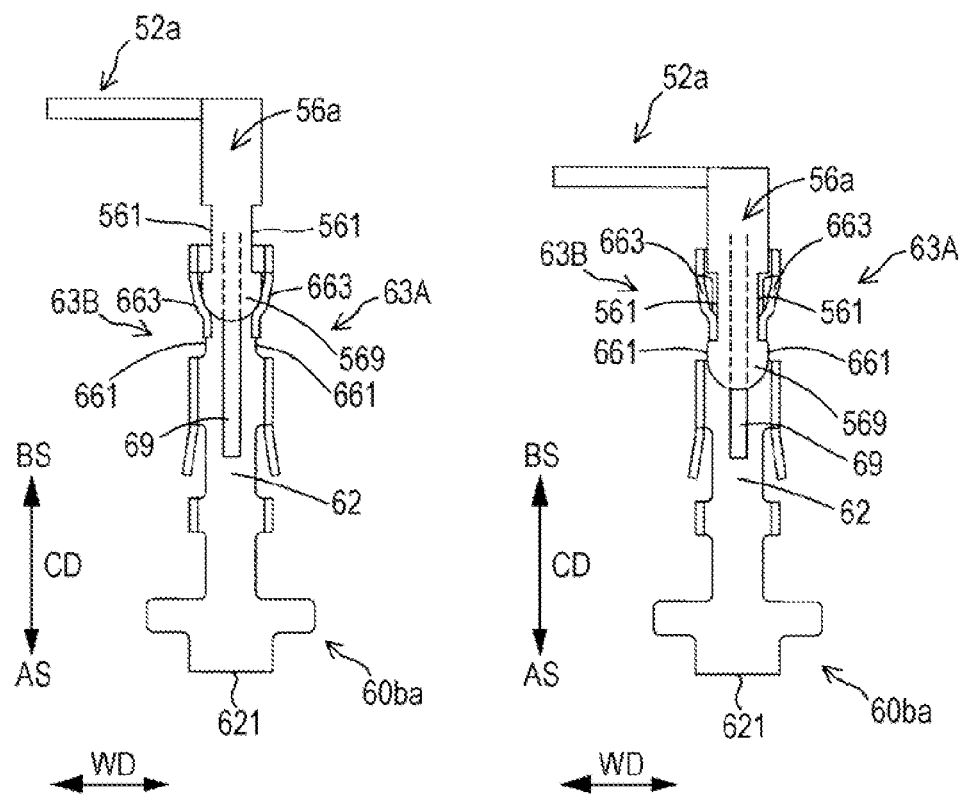
FIG. 13 illustrates a connector terminal according to another embodiment and how the connector terminal and the second connection terminal are engaged.

FIG. 13 illustrates a connector terminal 52*a* according to another embodiment and how the connector terminal 52*a* and the second connection terminal 60*ba* are engaged. FIG. 13(*a*) illustrates the state immediately before the connector terminal 52*a* and the second connection terminal 60*ba* are engaged. FIG. 13(*b*) illustrates the state in which the connector terminal 52*a* and the second connection terminal 60*ba* are engaged. The connector terminal 52*a* may be used as a component of the sensor 200 in place of each connector terminal 52 (FIG. 1) of the above-described embodiment. The connector terminal 52*a* differs from the connector terminal 52 of the above-described embodiment in that the other end portion 56*a* includes connector-terminal engagement portions 561. The structures of other portions of the connector terminal 52*a* are similar to as those of the connector terminal 52. Therefore, similar portions are denoted by the same reference numerals and description thereof is omitted.

The other end portion 56*a* of the connector terminal 52*a* includes the connector-terminal engagement portions 561 at the front side AS. The other end portion 56*a* has an oblong shape and extends in the axial direction CD. The connector-terminal engagement portions 561 are portions that engage with the connection-terminal engagement portions 663. The connector-terminal engagement portions 561 are recessed from the side surfaces of the other end portion 56*a*. The connector-terminal engagement portions 561 are on the back side BS of a front end portion 569.

The other end portion 56*a* is inserted into the space between the first and second side portions 63A and 63B from the back side BS of the second connection terminal 60*ba*. At this time, as illustrated in FIG. 13(*a*), the front end portion 569 pushes the connection-terminal engagement portions 663 away from each other in the width direction WD. Then, when the front end portion 569 passes the connection-terminal engagement portions 663 and reaches the holes 661, as illustrated in FIG. 13(*b*), the connection-terminal engagement portions 663 are inserted into the connector-terminal engagement portions 561, which are recesses. Thus, the connection-terminal engagement portions 663 and the connector-terminal engagement portions 561 engaged with each other in the axial direction CD. Owing to this engagement, the connection terminal 60*ba* is restrained from being moved toward the front side AS. In the state illustrated in FIG. 13(*b*), the connector contact portion 69 and the other end portion 56*a* are electrically connected to each other by being in contact with each other. As described above, since the connection-terminal engagement portions 663 and the connector-terminal engagement portions 561 are engaged with each other in the axial direction CD, the risk that the connection terminal 60*ba* will be moved toward the front side AS and become separated from the connector terminal 52*a* can be reduced. Accordingly, the electrical connection between the other end portion 56*a* and the connector contact portion 69 can be reliably maintained. Although the connector-terminal engagement portions 561 of the connector terminal 52*a* that is electrically connected to the second connection terminal 60*ba* are described, similar to the connector terminal 52*a*, connector terminals that are electrically connected to the other connection terminals (first, third, fourth, and fifth connection terminals) are also provided with the connector-terminal engagement portions 561. In addition, although the connector-terminal engagement portions 561 are recesses, the shape thereof is not limited to this as long as the connection-terminal engagement portions 663 can be inserted and engaged with the connector engagement portions. For example, the connector-terminal engagement portions 561 may instead be through holes that extend in the width direction WD.

D. Modifications

The present invention is not limited to the above-described examples and embodiments, and may be implemented in various forms without departing from the gist thereof.

D-1. First Modification:

In the above-described embodiment, the separator 30 and the base 40 are integrally formed of the same resin material (integrally molded) without using an adhesive or mechanical bonding means. However, the present invention is not limited to this as long as the separator 30 is made of a resin material. For example, the base 40 may be formed of a metal such as stainless steel. Alternatively, for example, the base 40 may be formed of a resin material different from the material of the separator 30. In the above-described embodiment, the connector terminals 52 are attached to the base 40 by being insert-molded in the base 40. However, the attachment method is not limited to this, and the connector terminals 52 may instead be attached to the base 40 by another attaching method. For example, the connector terminals 52 may be press-fitted to the base 40, or attached to the base 40 with an adhesive or the like.

D-2. Second Modification

In the above-described embodiment, the base 40 and the separator 30 are integrally formed of the same resin material (integrally molded) without using an adhesive or mechanical bonding means. However, the base 40 and the separator 30 may instead be integrally formed (integrally molded) by, for example, co-injection molding by using different resin materials.

D-3. Third Modification

In the above-described embodiment, as illustrated in FIG. 4, the connection terminals 60 include the inner extending portions 64. However, the connection terminals 60 need not include the inner extending portions 64 as long as the connection terminals 60 include the frame main bodies 62 and the spring portions 65 and 65a that form the element contact portions 67.

D-4. Fourth Modification

In the above-described embodiment, as illustrated in FIG. 3, the detector element 20 includes the first to fifth metal terminal portions 24a to 24e. However, the present invention is not limited to this as long as two or more metal terminal portions 24 are provided on one principal surface 20fa (20fb).

The present invention is not limited to the above-described embodiments, examples, and modifications and may be embodied in various forms within the gist thereof. For example, the technical features of the embodiments, examples, and modifications corresponding to the technical features according to the aspects described in the Summary of the Invention section may be replaced or combined as appropriate to solve some or all of the above-described problems or obtain some or all of the above-described effects. The technical features may also be omitted as appropriate unless they are described as being essential in this specification.

REFERENCE CHARACTERS LIST

- 10: terminal accommodation unit
- 15: attachment
- 16: metal shell
- 17: protector
- 18: outer protector
- 19: inner protector
- 20: detector element
- 20fa: first plate surface
- 20fb: second plate surface
- 21: detecting portion
- 22: element back portion
- 24: metal terminal portion
- 24a: first metal terminal portion
- 24b: second metal terminal portion
- 24c: third metal terminal portion
- 24d: fourth metal terminal portion
- 24e: fifth metal terminal portion
- 28: element layer
- 29: heater layer
- 30: separator
- 31: bottom portion
- 34: accommodation space
- 34a: first accommodation space
- 34b: second accommodation space
- 34c: third accommodation space
- 34d: fourth accommodation space
- 34e: fifth accommodation space
- 34f: sixth accommodation space
- 35: partition wall
- 35g: chamfered portion
- 35p: corner portion
- 38: groove
- 40: base
- 41: main body
- 44: side portion
- 50: connector portion
- 52, 52a: connector terminal
- 54: one end portion
- 56: other end portion
- 58: opening
- 60: connection terminal
- 60a: first connection terminal
- 60b, 60ba: second connection terminal
- 60c: third connection terminal
- 60d: fourth connection terminal
- 60e: fifth connection terminal
- 61, 61a: element contact portion
- 62: frame main body
- 63, 63a: protruding portion
- 63A: first side portion
- 63B: second side portion
- 64, 64a: inner extending portion
- 65, 65a: spring portion
- 67: element contact portion
- 68: retaining portion
- 69: connector contact portion
- 80: sealing member
- 85: connecting member
- 90: detecting-portion protecting layer
- 139: ceramic sleeve
- 157: crimping ring
- 158: sealing member
- 159: sealing member
- 162: groove portion
- 164: back portion
- 167: front-side outer peripheral portion
- 168: back-side outer peripheral portion
- 169: ledge portion
- 171: ceramic sleeve
- 173: powder-filled layer
- 175: ceramic holder
- 200: sensor
- 411: groove 561: connector-terminal engagement portion
621: front end portion
624: back end portion
661: hole
663: connection-terminal engagement portion
O: axis
CD: axial direction
BS: back side
AS: front side

What is claimed is:

1. A sensor comprising:
a detector element that extends in an axial direction and has a shape of a plate having two opposing principal surfaces, the detector element including a detecting portion at a front side in the axial direction and an element back portion at a back side in the axial direction, the detecting portion detecting a specific gas component contained in measurement target gas, the element back portion having two or more electrical connection terminal portions formed on one of the principal surfaces;
two or more connection terminals which each include an oblong frame main body that extends in the axial direction and an element contact portion that is bent at a front end portion of the frame main body so as to extend toward the back side and that is electrically connected to a corresponding one of the electrical connection terminal portions;
a separator that accommodates the connection terminals and the element back portion; and
a base that surrounds an outer periphery of the separator,
wherein the separator includes a partition wall that is made of a resin material and completely partitions a plurality of accommodation spaces from each other, and
wherein the accommodation spaces include an element accommodation space that accommodates portions of the element contact portions and the element back portion, and a plurality of terminal accommodation spaces which each accommodate one of the two or more frame main bodies.

2. The sensor according to claim 1,
wherein the base is made of a resin material,
wherein the base includes a bottom portion at the back side in the axial direction and a side portion that extends from a peripheral edge of the bottom portion toward the front side in the axial direction so as to surround a radial periphery of the separator, and
wherein the partition wall and the side portion are connected directly.

3. The sensor according to claim 1, wherein the base and the separator are integrally formed of the resin material.

4. The sensor according to claim 1, wherein the partition wall has a thickness that is constant in cross section orthogonal to the axial direction.

5. The sensor according to claim 1, further comprising:
connector terminals for transmitting a detection signal output from the detector element to outside,
wherein the base includes a connector portion that extends in a direction crossing the axial direction and that accommodates one end portion of each connector terminal, and
wherein the other end portion of each connector terminal is electrically connected to a corresponding one of the connection terminals in a corresponding one of the accommodation spaces.

6. The sensor according to claim 5,
wherein the other end portion of each connector terminal includes a connector-terminal engagement portion having a recess or a hole, and
wherein each connection terminal includes a connection-terminal engagement portion that is inserted into the recess or the hole so as to be engaged with the connector-terminal engagement portion.

7. The sensor according to claim 5, wherein the connector terminals are embedded in the base so that the connector terminals and the base are bonded together.

8. The sensor according to claim 1,
wherein the base is made of a resin material,
wherein the base includes a bottom portion at the back side in the axial direction and a side portion that extends from a peripheral edge of the bottom portion toward the front side in the axial direction so as to surround a radial periphery of the separator, and
wherein the partition wall and the side portion are connected indirectly with a component other than the base and the component provided therebetween.

* * * * *